United States Patent
Yajima et al.

[11] Patent Number: 5,972,373
[45] Date of Patent: Oct. 26, 1999

[54] TASTE MASKING PHARMACEUTICAL COMPOSITION FOR ORAL ADMINISTRATION

[75] Inventors: Toshio Yajima; Kuniaki Ishii; Shigeru Itai; Masami Nemoto; Kouji Suetake; Nobuyoshi Tsukui, all of Tokyo, Japan

[73] Assignee: Taisho Pharmaceutical Co., Ltd., Tokyo, Japan

[21] Appl. No.: 08/945,822

[22] PCT Filed: Apr. 30, 1996

[86] PCT No.: PCT/JP96/01179

§ 371 Date: Oct. 31, 1997

§ 102(e) Date: Oct. 31, 1997

[87] PCT Pub. No.: WO96/34628

PCT Pub. Date: Nov. 7, 1996

[30] Foreign Application Priority Data

May 2, 1995 [JP] Japan ................................. 7-108338

[51] Int. Cl.$^6$ .............................. A61K 9/10; A61K 9/16; A61K 47/26; A61K 47/32
[52] U.S. Cl. .......................... 424/439; 424/486; 424/487; 424/501; 514/974
[58] Field of Search ................................... 424/486, 457, 424/464–465, 468–470, 501, 439; 514/974

[56] References Cited

U.S. PATENT DOCUMENTS

| | | |
|---|---|---|
| 3,034,897 | 5/1962 | Kuhrt et al. . |
| 3,034,898 | 5/1962 | Kuhrt et al. . |
| 3,673,106 | 6/1972 | Jones et al. . |
| 4,315,041 | 2/1982 | Fukuda et al. . |
| 4,327,077 | 4/1982 | Puglia et al. ............................. 424/38 |
| 5,707,646 | 1/1998 | Yajima et al. . |

FOREIGN PATENT DOCUMENTS

| | | | |
|---|---|---|---|
| 0 069 097 | 1/1983 | European Pat. Off. | ......... A61K 9/50 |
| 0 101 418 | 2/1984 | European Pat. Off. | ......... A61K 9/10 |
| 0 630 233 | 9/1996 | European Pat. Off. | ......... A61K 9/16 |
| 49-81526 | 8/1974 | Japan . | |
| 57-203010 | 12/1982 | Japan | ............... A61K 9/20 |

*Primary Examiner*—Edward J. Webman
*Attorney, Agent, or Firm*—Sughrue, Mion, Zinn, Macpeak & Seas, PLLC

[57] ABSTRACT

[Object] To provide a composition for oral administration which is excellent in masking a taste of an unpleasant tasting drug and in bioavailability.

[Constitution] A composition for oral administration comprising an unpleasantly tasting drug, a high polymer soluble in the stomach and a monoglyceride in the β-crystal form.

5 Claims, No Drawings

TASTE MASKING PHARMACEUTICAL COMPOSITION FOR ORAL ADMINISTRATION

This application is a 371 of PCT/JP96/001179 Apr. 30, 1996.

TECHNICAL FIELD

The present invention relates to a pharmaceutical composition of an unpleasantly tasting drug, and more particularly, it relates to a composition for oral administration which is excellent in masking a taste of an unpleasantly tasting drug and has a good bioavailability.

BACKGROUND ART

There have been hitherto found various preparations for masking tastes of unpleasantly tasting drugs.

For example, Japanese Patent Kokai 49-81526 discloses a method which comprises dissolving a macrolide antibiotic in an inert volatile organic solvent wherein a wall polymer selected from the group consisting of polyvinylacetal diethylaminoacetate (hereinafter referred to as "AEA"), cellulose acetate dibutylaminohydroxypropyl ether, aminoalkylmethacrylate copolymer E (trade name; Eudragit E) and ethyl cellulose and at least one selected from the group consisting of a wax, a higher fatty acid and a salt insoluble in the higher fatty acid are dissolved or dispersed; spray-drying the solution; and collecting the resulting encapsulated particles of the macrolide antibiotic.

On the other hand, EP Patent No. 37740 discloses a pharmaceutical preparation having an improved stability and content uniformity of drugs, and this preparation can be applied to mask an unpleasant taste, but has a drawback of a bad dissolution because waxes only are used for masking.

As an example of a pharmaceutical mixture for masking a taste of an unpleasantly tasting basic drug, EP Patent No. 69097 discloses that a dry powder for a pharmaceutical mixture comprising an encapsulated bad tasting drug in a form insoluble at high pH.

In addition, EP Patent No. 101418 discloses a pharmaceutical mixture preparation with controlled release of an active substance which includes masking of bad taste and stability increasing of the active substance characterized in that it contains an encapsulated active substance in combination with 40–99% of a release controlling substance, examples of which are a carbohydrate, a carbohydrate-related compound and a mixture of such compounds.

In the past, however, since an inert volatile organic solvent (e.g. methylene chloride, chloroform, cyclohexane, carbon tetrachloride, methylethylketone, acetone, methyl alcohol or isopropyl alcohol) should be used for dissolving coating agents, a drying step for removal of the solvent is required. As a result, the coating layer becomes porous, and the drying step requires a lot of time, equipment, labor, cost, etc. In addition, this step has risks such as inflammation and explosion in work, and the product might contain the residual inert volatile organic solvent which is feared to affect human health, therefore, it has a problem for safety.

In order to mask a taste of an unpleasantly tasting basic drug without using the inert volatile organic solvent, the present inventors disclose in EP. Patent No. 630233 a composition for oral administration comprising a complex formed by dispersing or dissolving the drug and a high polymer soluble in the stomach in a substance having a low melting point of 40 to 120° C., a sugar-alcohol and a basic oxide.

DISCLOSURE OF THE INVENTION

The present inventors researched variously in order to obtain compositions for oral administration for masking a taste of an unpleasantly tasting drug with a good bioavailability. Monoglycerides having a low melting point are superior for making elaborate film, and are easily soluble in the intestines, therefore, they are good materials for formulating.

High polymers soluble in the stomach are useful as materials which are insoluble or hardly soluble in the mouth (pH 5–8), being easily soluble in the stomach (pH 1–4).

Monoglycerides are found to exist in some crystal forms which have different melting points each other, and usually the monoglyceride in the composition for oral administration is in the α-crystal form immediately after the preparation. The present inventors have found that when a monoglyceride exists in the α-crystal form, the unpleasant tastes of drugs can not be sufficiently masked for a long term, but unexpectedly, when a monoglyceride exists in the β-crystal form, the unpleasant taste of drugs can be masked sufficiently for long term. Furthermore, the present inventors have found that a combination of a monoglyceride in the -crystal form and a high polymer soluble in the stomach not only can mask the taste of an unpleasantly tasting drugs effectively, but also can make it possible to rapidly dissolve the drug in the stomach, and has a good bioavailability. The present invention has been accomplished by the findings. Accordingly, the present invention relates to a composition for oral administration comprising an unpleasantly tasting drug, a high polymer soluble in the stomach and a monoglyceride in the β-crystal form.

For transition of the α-crystal form of monoglyceride into the β-crystal form thereof, for example, there is a method which comprises tumbling or shaking the granules containing a monoglyceride at a temperature of from 25 to 60° C., preferably 35 to 45° C.

The unpleasantly tasting drug to be used in the present invention includes macrolide antibiotics (e.g. erythromycin, clarithromycin, kitasamycin, josamycin, midecamycin, roxithromycin or azithromycin), β-lactam antibiotics (e.g. penicillin derivatives or cephalosporin derivatives), tetracycline antibiotics, psychotropic drugs (e.g. chlorpromazine), cardiotonics (e.g. digitoxin), antipyretic drugs (e.g. sulpyrine), anti-ulcer drugs (e.g. cimetidine), etc. The amount of the drug is from 1 to 90% by weight based on the composition for oral administration, preferably 1 to 60% by weight.

The monoglyceride to be used in the present invention includes glyceryl monostearate, glyceryl monopalmitate, glyceryl monooleate, glyceryl monocaprylate, glyceryl monocaprate, glyceryl monolaurate, etc., preferably glyceryl monostearate.

The polymer soluble in the stomach to be used in the present invention includes Eudragit E, AEA, a mixture thereof, etc., preferably Eudragit E.

The amount of the monoglyceride is from 1 to 95% by weight based on the composition for oral administration, preferably 20 to 90% by weight. The amount ratio of the monoglyceride to the polymer soluble in the stomach is from 99:1 to 30:70, preferably 90:10 to 50:50.

The composition for oral administration of the present invention can be prepared, for example, by the following method. A high polymer soluble in the stomach is dispersed or dissolved in a monoglyceride which is heated to a temperature equal to or higher than the melting point to give a mixture. An unpleasantly tasting drug is granulated using the above mixture at a high temperature, and cooled, followed by tumbling or shaking at a temperature of 25 to 60° C., preferably 35 to 45° C. to transit the α-crystal form of the monoglyceride into the β-crystal thereof in a short time, whereby the composition of the present invention can be prepared. Examples of the granulation are melting granulation, heating granulation and spraying granulation.

The composition for oral administration of the present invention can be formulated in the unit dose forms such as granules, powders, capsules, tablets, dry syrups, preferably dry syrups.

For the preparation of the composition for oral administration, if desired, ordinary additives for the preparations of medicines can be used, examples of which are an excipient, a disitegrant, a binder, a lubricant, an anti-oxidant, a coating agent, a colorant, a corrigent, a surfactant and a plasticizer.

The excipient includes mannitol, xylitol, sorbitol, maltitol, dextrose, sucrose, lactose, crystalline cellulose, crystalline cellulose-sodium carboxymethyl cellulose, calcium hydrogen phosphate, wheat starch, rice starch, corn starch, potato starch, sodium carboxymethyl starch, dextrin, α-cyclodextrin, β-cyclodextrin, carboxyvinyl polymer, light anhydrous silicic acid, titanium oxide, magnesium oxide, aluminum oxide, magnesium hydroxide, aluminum hydroxide, sodium hydrogen carbonate, magnesium aluminometasilicate, polyethylene glycol, medium chain fatty acid triglyceride, etc.

The disintegrant includes low substituted hydroxypropyl cellulose, carboxymethyl cellulose, calcium carboxymethyl cellulose, sodium carboxymethyl cellulose, croscarmellose sodium A-type (Ac-di-sol), starch, crystalline cellulose, hydroxypropyl starch, partly pregelatinized starch, etc.

The binder includes methyl cellulose, hydroxypropyl cellulose, hydroxypropylmethyl cellulose, polyvinylpyrrolidone, gelatin, gum arabic, ethyl cellulose, polyvinyl alcohol, pullulan, pregelatinized starch, agar, tragacanth, sodium alginate, propyleneglycol alginate, etc.

The lubricant includes stearic acid, magnesium stearate, calcium stearate, polyoxyl stearate, cetanol, talc, hydrogenated caster oil, sucrose esters of fatty acid, dimethylpolysiloxane, microcrystalline wax, yellow beeswax, white beeswax, etc.

The anti-oxidant includes dibutylhydroxytoluene (BHT), propyl gallate, butylhydroxyanisol (BHA), α-tocopherol, citric acid, etc.

The coating agent includes hydroxypropylmethyl cellulose, hydroxypropyl cellulose, methyl cellulose, ethyl cellulose, hydroxypropylmethyl cellulose phthalate, hydroxypropylmethyl cellulose acetate succinate, carboxymethylethyl cellulose, cellulose acetate phthalate, polyvinylacetal diethylaminoacetate, aminoalkyl methacrylate copolymer, hydroxypropylmethyl cellulose acetate succinate, methacrylic acid copolymer, cellulose acetate trimellitate (CAT), polyvinyl acetate phthalate, shellac, etc.

The colorant includes tar dyestuff, titanium oxide, etc.

The corrigent includes citric acid, adipic acid, ascorbic acid, menthol, etc.

The surfactant includes polyoxyethylene hardened castor oil, glyceryl monostearate, sorbitan monostearate, sorbitan monopalmitate, sorbitan monolaurate, polyoxyethylene polyoxypropylene block copolymers, polysorbates, sodium laurylsulfate, macrogols, sucrose esters of fatty acids, etc.

The plasticizer includes triethyl citrate, triacetin, acetal, etc.

INDUSTRIAL APPLICABILITY

According to the present invention, the preparation for oral administration of unpleasantly tasting drugs makes it possible to continuously mask the unpleasant taste for a long term, and has an excellent bioavailability.

Furthermore, the preparation for oral administration obtained by the present invention does not give the unpleasant taste even when suspended in water and then continuously stored at room temperature for 14 days, and has an excellent bioavailability, therefore, it can be easily applied orally to infants in the form of dry-syrups for pediatrics.

BEST MODE FOR CARRYING OUT THE INVENTION

The present invention is illustrated in more detail by the following examples and experiments.

EXAMPLE 1

600 g of glyceryl monostearate was melted at about 100° C., and 100 g of Eudragit E was dispersed and dissolved therein. In the mixture was further dispersed 300 g of erythromycin, followed by spray-cooling granulation using a spray-dryer at an inlet temperature of 80° C. at a rotary disk rotation rate of 20000 rpm. Then, the resulting granules were tumbled and shaken by a VG coater (Kikusui Manufacturing Ltd.) at a jacket temperature of 40° C. at a rotation rate of 15 rpm for 2 hours to give about 950 g of a powder wherein the glyceryl monostearate was in the β-crystal form.

EXAMPLE 2

600 g of glyceryl monostearate was melted at about 100° C., and 100 g of Eudragit E was dispersed and dissolved therein. In the mixture was further dispersed 300 g of clarithromycin, followed by spray-cooling granulation using a spray-dryer at an inlet temperature of 80° C. at a rotary disk rotation rate of 20000 rpm. Then, the resulting granules were tumbled and shaken by a VG coater (Kikusui Manufacturing Ltd.) at a jacket temperature of 40° C. at a rotation rate of 15 rpm for 2 hours to give about 950 g of a powder wherein the glyceryl monostearate was in the β-crystal form.

EXAMPLE 3

To 333 g of the powder of Example 1 were added 300 g of sorbitol, 20 g of magnesium oxide and 347 g of starch, followed by homogeneous mixing. The mixture was subjected to fluidized bed granulation with water to give granules.

EXAMPLE 4

To 333 g of the powder of Example 1 were added 500 g of mannitol, 15 g of magnesium oxide and 152 g of starch, followed by homogeneous mixing. The resulting mixture was subjected to fluidized bed granulation with water to give granules.

EXAMPLE 5

To 333 g of the powder of Example 1 were added 450 g of xylitol, 10 g of magnesium oxide and 162 g of starch, followed by homogeneous mixing. The resulting mixture was subjected to fluidized bed granulation with water to give granules.

EXAMPLE 6

To 333 g of the powder of Example 2 were added 300 g of sorbitol, 300 g of mannitol, 5 g of magnesium oxide, 10 g of sodium carboxymethyl cellulose and 52 g of crystalline cellulose, followed by homogeneous mixing. The resulting mixture was subjected to fluidized bed granulation with water to give granules.

EXAMPLE 7

To 333 g of the powder of Example 1 were added 300 g of sorbitol, 300 g of mannitol, 10 g of sodium carboxymethyl cellulose and 47 g of starch, followed by homogeneous mixing. The resulting mixture was subjected to fluidized bed granulation using the separately-prepared suspension of 10 g of magnesium oxide in water as a binding solvent to give granules.

EXAMPLE 8

To 333 g of the powder of Example 2 were added 300 g of sorbitol, 10 g of sodium carboxymethyl cellulose and 347 g of starch, followed by homogeneous mixing. The resulting mixture was subjected to fluidized bed granulation using the separately-prepared suspension of 10 g of magnesium oxide in water as a binding solvent to give granules.

EXAMPLE 9

To 333 g of the powder of Example 2 were added 400 g of sorbitol, 229 g of xylitol, 10 g of sodium carboxymethyl cellulose, 5 g of magnesium oxide, 20 g of hydroxylpropyl cellulose and 3 g of saccharin sodium, followed by homogeneous mixing. The mixture was subjected to fluidized bed granulation using water as a granulating solvent to give granules, 1 g of which was then suspended in about 5 ml of water, whereby a syrup was obtained.

EXAMPLE 10

To 333 g of the powder of Example 2 were added 300 g of sorbitol, 100 g of mannitol, 100 g of xylitol, 100 g of maltitol, 10 g of sodium carboxymethyl cellulose, 20 g of magnesium oxide, 14 g of starch, 20 g of hydroxylpropyl cellulose and 3 g of saccharin sodium, followed by homogeneous mixing. The resulting mixture was subjected to fluidized bed granulation using water as a granulating solvent to give a dry-syrup containing 10% clarithromycin.

EXAMPLE 11

To 333 g of the powder of Example 1 were added 500 g of mannitol, 20 g of magnesium oxide, 125 g of starch, 20 g of hydroxylpropyl cellulose and 2 g of sodium carboxymethyl cellulose, followed by homogeneous mixing. The resulting mixture was subjected to fluidized bed granulation with water to give granules.

EXAMPLE 12

600 g of glyceryl monostearate was melted at about 100° C., and 100 g of Eudragit E was dispersed and dissolved therein. In the mixture was further dispersed 300 g of erythromycin, followed by spray-cooling granulation using a spray-dryer at an inlet temperature of 80° C. at a rotary disk rotation rate of 20000 rpm. Then, the resulting granules were tumbled and shaken by a VG coater (Kikusui Manufacturing Ltd.) at a jacket temperature of 45° C. at a rotation rate of 15 rpm for an hour to give about 950 g of a powder wherein the glyceryl monostearate was in the β-crystal form. To 333 g of the resulting powder were added 300 g of sorbitol, 300 g of mannitol, 10 g of sodium carboxymethyl cellulose and 47 g of starch, followed by homogeneous mixing. The resulting mixture was subjected to fluidized bed granulation using the separately-prepared suspension of 10 g of magnesium oxide in water as a binding solvent to give granules.

EXAMPLE 13

600 g of glyceryl monogstearate was melted at about 100° C., and 100 g of Eudragit E was dispersed and dissolved therein. In the mixture was further dispersed 300 g of erythromycin, followed by spray-cooling granulation using a spray-dryer at an inlet temperature of 70° C. at a rotary disk rotation rate of 15000 rpm. Then, the granules were tumbled and shaken by a VG coater (Kikusui Manufacturing Ltd.) at a jacket temperature of 35° C. at a rotation rate of 15 rpm for 3 hours to give about 950 g of a powder wherein the glyceryl monostearate was in the β-crystal form. To 333 g of the resulting powder were added 300 g of mannitol, 10 g of sodium carboxymethyl cellulose and 347 g of starch, followed by homogeneous mixing. The resulting mixture was subjected to fluidized bed granulation using the separately-prepared suspension of 10 g of magnesium oxide in water as a binding solvent to give granules.

Control Example 1

600 g of glyceryl monostearate was melted at about 100° C., and 100 g of Eudragit E was dispersed and dissolved therein. In the mixture was further dispersed 300 g of erythromycin, followed by spray-cooling granulation using a spray-dryer at an inlet temperature of 80° C. at a rotary disk rotation rate of 20000 rpm to give about 950 g of a powder wherein the glyceryl monostearate was in the α-crystal form.

Control Example 2

To 333 g of the powder of Control Example 1 were added 300 g of sorbitol, 20 g of magnesium oxide and 347 g of starch, followed by homogeneous mixing. The mixture was subjected to fluidized bed granulation with water to give granules.

Experiment 1:

[Test preparations]

Compositions for oral administration obtained in Examples 1 and 3 to 13, and Control Examples 1 and 2.

[Test method]

2 g of each composition suspended in 5 ml of water was stored at room temperature, and administered orally to 10 healthy adults to evaluate bitter taste. The measurement was carried out immediately after the preparation, after 3 days, 7 days and 14 days, and the evaluation was carried out immediately after administration, after one minute and 10 minutes. The judges were assigned from 5 points according to the following scale: 0=not sensibly bitter, 1=slightly sensibly bitter, 2=bitter to some extent, 3=bitter, 4=tolerably bitter, and 5=intolerably bitter.

[Results]

Results are shown by the mean taste rating of 10 adults in Table 1 below. The composition obtained in each of Examples was found better in masking bitter taste for a long term than those of Control examples.

TABLE 1

|  | Immediately after | | | after 3 days | | | after 7 days | | | after 14 days | | |
| --- | --- | --- | --- | --- | --- | --- | --- | --- | --- | --- | --- | --- |
|  | im'ly after | 1 min. | 3 mins. | im'ly after | 1 min. | 3 mins. | im'ly after | 1 min. | 3 mins. | im'ly after | 1 min. | 3 mins. |
| Con. 1 | 0 | 0 | 0 | 2 | 2 | 1 | 4 | 4 | 3 | 5 | 5 | 5 |
| Con. 2 | 0 | 0 | 0 | 0 | 1 | 1 | 2 | 3 | 2 | 4 | 4 | 4 |
| Ex. 1 | 0 | 0 | 0 | 1 | 1 | 1 | 1 | 2 | 1 | 1 | 2 | 1 |
| Ex. 2 | 0 | 0 | 0 | 0 | 0 | 0 | 0 | 0 | 0 | 0 | 0 | 0 |
| Ex. 3 | 0 | 0 | 0 | 0 | 0 | 0 | 0 | 0 | 0 | 0 | 0 | 0 |
| Ex. 4 | 0 | 0 | 0 | 0 | 0 | 0 | 0 | 0 | 0 | 0 | 0 | 0 |
| Ex. 5 | 0 | 0 | 0 | 0 | 0 | 0 | 0 | 0 | 0 | 0 | 0 | 0 |
| Ex. 6 | 0 | 0 | 0 | 0 | 0 | 0 | 0 | 0 | 0 | 0 | 0 | 0 |
| Ex. 7 | 0 | 0 | 0 | 0 | 0 | 0 | 0 | 0 | 0 | 0 | 0 | 0 |
| Ex. 8 | 0 | 0 | 0 | 0 | 0 | 0 | 0 | 0 | 0 | 0 | 0 | 0 |
| Ex. 9 | 0 | 0 | 0 | 0 | 0 | 0 | 0 | 0 | 0 | 0 | 0 | 0 |
| Ex. 10 | 0 | 0 | 0 | 0 | 0 | 0 | 0 | 0 | 0 | 0 | 0 | 0 |
| Ex. 11 | 0 | 0 | 0 | 0 | 0 | 0 | 0 | 0 | 0 | 0 | 0 | 0 |
| Ex. 12 | 0 | 0 | 0 | 0 | 0 | 0 | 0 | 0 | 0 | 0 | 0 | 0 |
| Ex. 13 | 0 | 0 | 0 | 0 | 0 | 0 | 0 | 0 | 0 | 0 | 0 | 0 | note;
im'ly = immediately, Con. = Control Example, Ex. = Example.

Experiment 2:
[Test preparations]
Compositions for oral administration obtained in Examples 1 and 3 to 13.
[Test method]
The dissolution test of each 1 g of the compositions was carried out according to a method of Japanese Pharmacopoeia, 11th edition, using an acetic acid buffer solution (pH 4.0) as a dissolution medium at a paddle rotation rate of 100 rpm, and the dissolution ratio after 10 minutes was measured.
[Results]
Results are shown in Table 2 below. Each composition Examples showed good dissolution ratio.

TABLE 2

|  | 10 mins. |  | 10 mins. |
| --- | --- | --- | --- |
| Example 1 | 100 | Example 8 | 100 |
| Example 2 | 100 | Example 9 | 100 |
| Example 3 | 100 | Example 10 | 100 |
| Example 4 | 100 | Example 11 | 100 |
| Example 5 | 100 | Example 12 | 100 |
| Example 6 | 100 | Example 13 | 100 |
| Example 7 | 100 |  |  |

We claim:

1. A pharmaceutical composition for oral administration for masking a bitter taste comprising an unpleasantly tasting drug, a polymer selected from the group consisting of polyvinylacetal diethylaminoacetate, aminoalkylmethacrylate copolymer E or a mixture thereof, and a monoglyceride in the β-crystal form, said composition is produced by the method which comprises the steps of:

dispersing or dissolving said polymer in a monoglyceride which is heated to a temperature equal to or higher than the melting point;

granulating an unpleasantly tasting drug using the resulting mixture of polymer and monoglyceride;

cooling the granules; and and causing the α-crystal form of monoglyceride in the granules to convert into the β-crystal thereof.

2. The composition for oral administration according to claim 1 wherein the amount of the monoglyceride is from 1 to 95% by weight based on the composition for oral administration, and the amount ratio of the monoglyceride to the high polymer is from 99:1 to 30:70.

3. The composition for oral administration according to claim 1 wherein the high polymer is polyvinylacetal diethylaminoacetate, aminoalkylmethacrylate copolymer E or a mixture thereof, and the monoglyceride is glyceryl monostearate.

4. The composition for oral administration according to claim 1 of which unit dosage form is a dry syrup.

5. A method for masking a taste of an unpleasant tasting drug, comprising using a high polymer selected from the group consisting of polyvinylacetal diethylaminoacetate, aminoalkylmethacrylate copolymer E or a mixture thereof, and a monoglyceride in the β-crystal form, wherein said method comprises the steps of:

dispersing or dissolving said polymer in a monoglyceride which is heated to a temperature equal to or higher than the melting point;

granulating an unpleasantly tasting drug using the resulting mixture of polymer and monoglyceride;

cooling the granules; and causing the α-crystal form of monoglyceride in the granules to convert into the β-crystal thereof.

* * * * *